US00PP15443P2

(12) United States Plant Patent
van Rijn

(10) Patent No.: US PP15,443 P2
(45) Date of Patent: Dec. 21, 2004

(54) *CALATHEA* PLANT NAMED 'TANJA'

(50) Latin Name: *Calathea roseo picta*
Varietal Denomination: Tanja

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 10/805,585

(22) Filed: Mar. 20, 2004

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database 2003/05, GTI Jouve Retrieval Software, Citation for 'Tanja'.*

* cited by examiner

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Calathea* plant named 'Tanja', characterized by its upright and broad outwardly spreading growth habit; broadly ovate leaf shape; upper leaf surfaces grayed green in color with dark green-colored margins; and lower leaf surfaces dark purple in color.

2 Drawing Sheets

Botanical classification/cultivar designation: *Calathea roseo picta* cultivar 'Tanja'.

BACKGROUND OF THE INVENTION

The present Invention relates to a new and distinct cultivar of *Calathea* plant, botanically known as *Calathea roseo picta,* and hereinafter referred to by the namae 'Tanja'.

The new *Calathea* is a naturally-occurring whole plant mutation of the *Calathea roseo picta* cultivar Rosy, disclosed in U.S. Plant Pat. No. 8,836. The new *Calathea* was discovered and selected by the Inventor as a single plant from within a population of plants of the cultivar Rosy in a controlled environment in Schipluiden, The Netherlands during the Fall, 2000. The selection of this plant was based on its attractive leaf coloration.

Asexual reproduction of the new cultivar by cuttings taken at Schipluiden, The Netherlands since the Fall, 2000, has shown that the unique features of this new *Calathea* are stable and reproduced true to type in successive generations.

SUMMARY OF THE INVENTION

Plants of the cultivar Tanja have not been observed under all possible environmental conditions. The phenotype may vary somewhat with variations in environment such as temperature and/or light intensity without, however, any variance in genotype.

The following traits have been repeatedly observed and are determined to be the unique characteristics of 'Tanja'. These characteristics in combination distinguish 'Tanja' as a new and distinct cultivar:

1. Upright and broad outwardly spreading growth habit.
2. Leaf shape, broadly ovate.
3. Upper leaf surfaces grayed green in color with dark green-colored margins.
4. Lower leaf surfaces dark purple in color.

Plants of the new *Calathea* are most similar to plants of the parent cultivar, Rosy. However plants of the new

*Calathea* differ primarily from plants of the cultivar Rosy in leaf coloration as plants of the cultivar Rosy have pink and green-colored leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new *Calathea.*

The photograph on the first sheet comprises a side perspective view of a typical plant of 'Tanja' grown in a container.

The photograph on the second sheet is a close-up view of the lower surface (top) and upper surface (bottom) of typical leaves of 'Tanja'.

DETAILED BOTANICAL DESCRIPTION

In the following description, color references are made to The Royal Horticultural Society Colour Chart, 2001 Edition, except where general terms of ordinary dictionary significance are used. Plants used for the above-mentioned photographs and botanical description were grown in Schipluiden, The Netherlands in a glass-covered greenhouse in containers during the winter. During the production of the plants, day temperatures were about 24° C., night temperatures were about 21° C. and light levels ranging from 2,000 to 3,000 lux. Plants used for the aforementioned photograph and following description were about one year old.

Botanical classification: *Calathea roseo picta* cultivar 'Tanja'.

Parentage: Naturally-occurring whole plant mutation of the *Calathea roseo picta* cultivar Rosy, disclosed in U.S. Plant Pat. No. 8,836.

Propagation:

*Type.*—By cuttings.

*Time to initiate roots, summer.*—About 84 days at 22° C.

*Time to initiate roots, winter.*—About 112 days at 22° C.

*Time to develop roots.*—About 252 days at 22° C.

*Root description.*—Main roots, fibrous; lateral roots, fine; dark brown in color.

Plant description:

*Form.*—Upright and broad outwardly spreading growth habit; freely clumping, leaves emerging from the base in a rosette.

*Plant height, soil level to top of plant plane.*—About 30 cm.

*Plant width.*—About 51 cm.

*Foliage description.*—Arrangement: Alternate, simple; typically three leaves per clump. Length: About 18.7 cm. Width: About 14.9 mm. Shape: Broadly ovate to almost orbicular. Apex: Abruptly acute. Base: Obtuse. Margin: Entire; undulate. Texture, upper and lower surfaces: Smooth, glabrous; slightly leathery. Luster, upper and lower surfaces: Dull. Venation pattern: Pinnate. Color: Developing foliage, upper surface: 148C; margin, 1.7 cm wide, darker than 147A. Developing foliage, lower surface: 187B; margin, 1.7 cm wide, N186C. Fully expanded foliage, upper surface: 191A to 191B to N138C; margin, 1.7 cm wide, darker than 139A. Fully expanded foliage, lower surface: N186C Venation, upper surface: Primary veins, 144A to 144B; secondary veins, 189A. Venation, lower surface: Primary veins, N186C tinted with dark yellow green; secondary veins, N186C. Petiole length: About 13.5 cm. Petiole diameter: About 5 mm. Geniculum length: About 2.6 mm. Geniculum diameter: About 4.5 mm. Wing length: About 5 cm. Wing diameter: About 4.5 mm. Color: Petiole: N186C; towards the base, 187C. Geniculum: N186C tinted with dark yellow green. Wing: 187A to 187B.

Flower description: Flower development has not been observed.

Disease/pest resistance: Under commercial production conditions, plants of the new *Calathea* have not been noted to be resistant to pathogens or pests common to *Calathea*.

Temperature tolerance: Plants of the new *Calathea* have been observed to tolerate temperatures from 10 to 30° C. in Schipluiden, The Netherlands.

It is claimed:

1. A new and distinct cultivar of *Calathea* plant named 'Tanja', as illustrated and described.

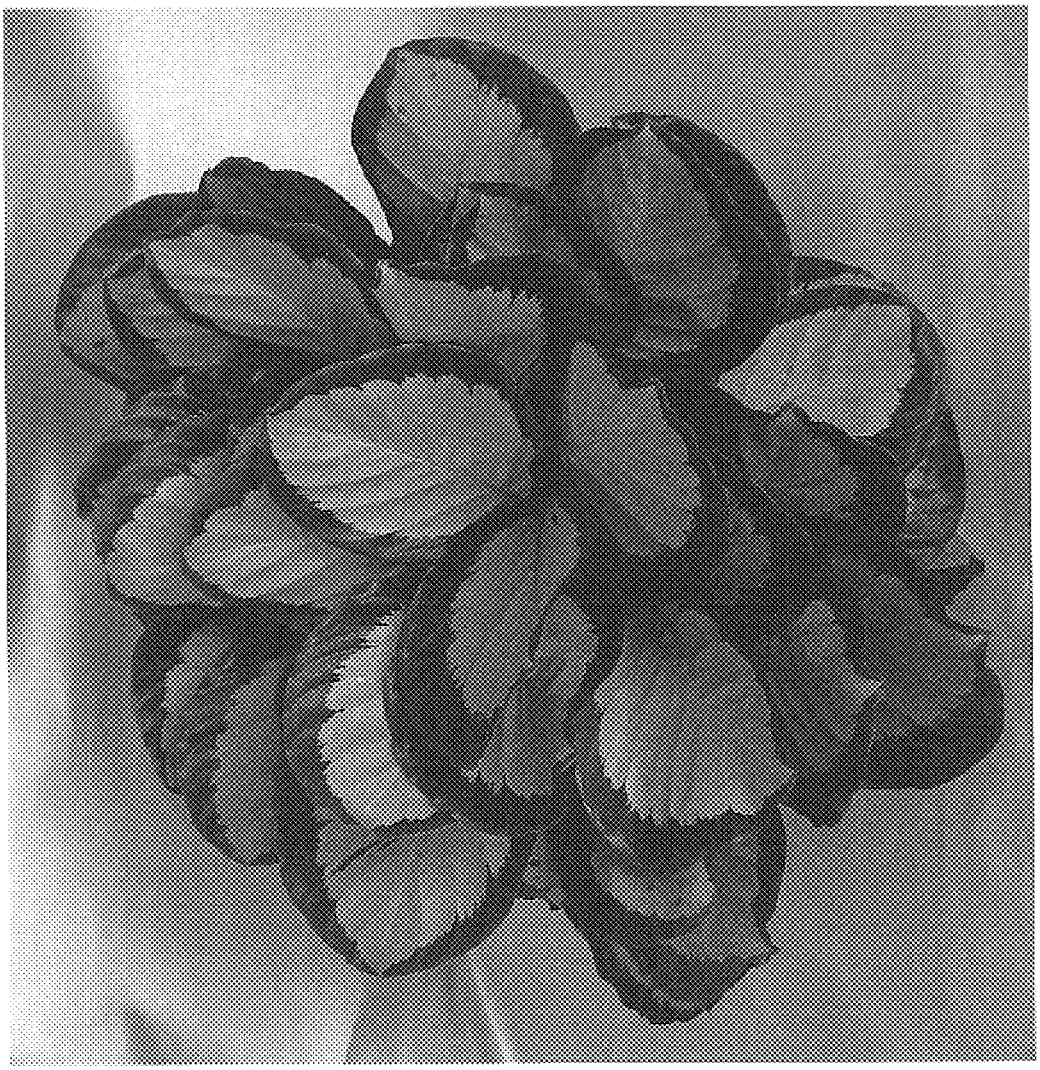

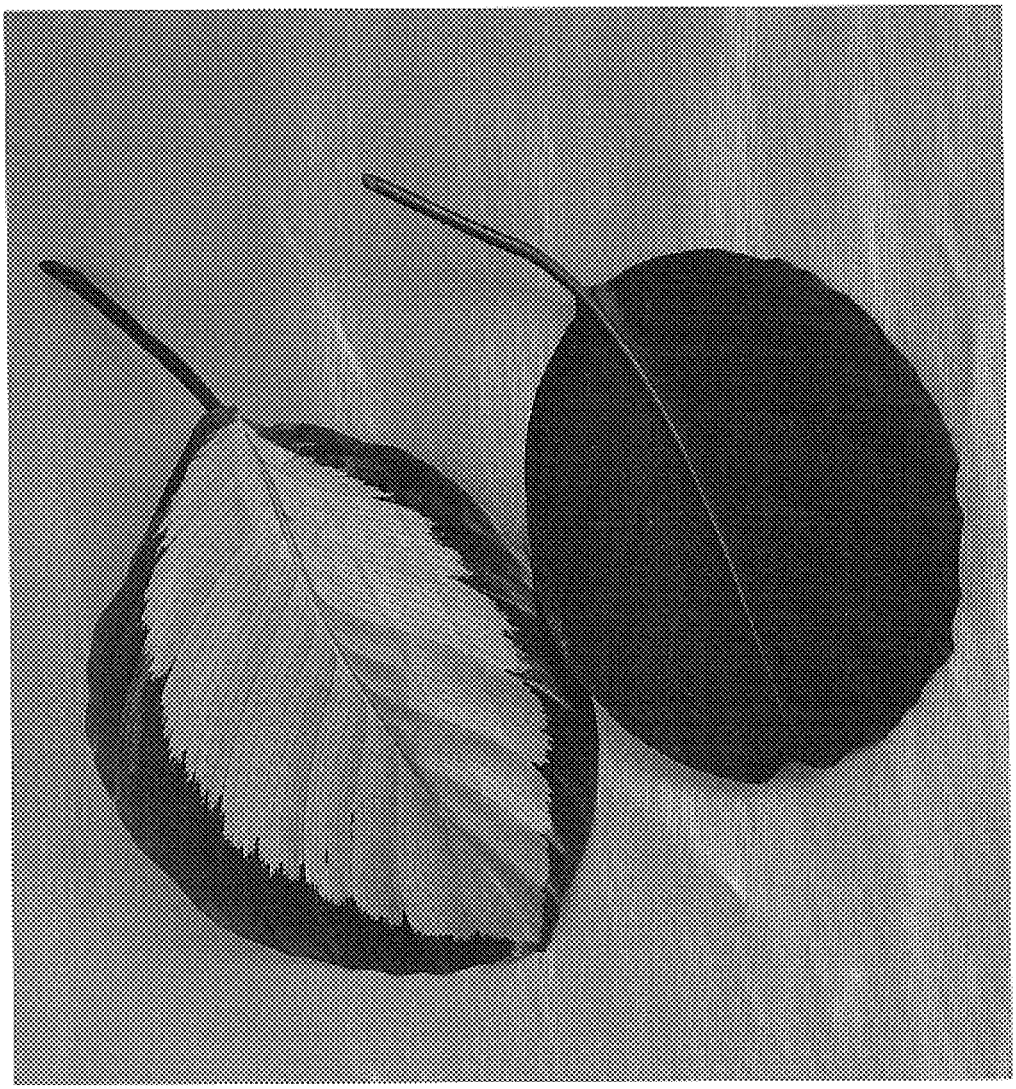

* * * * *